US00PP25292P2

(12) United States Plant Patent
Trees

(10) Patent No.: US PP25,292 P2
(45) Date of Patent: Feb. 17, 2015

(54) ***BRUGMANSIA* PLANT NAMED 'LITTLE ANGEL'**

(50) Latin Name: *Brugmansia sauveolens*
Varietal Denomination: Little Angel

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 123 days.

(21) Appl. No.: 13/986,609

(22) Filed: May 17, 2013

(51) Int. Cl.
*A01H 5/00* (2006.01)

(52) U.S. Cl.
USPC ..... Plt./226

(58) Field of Classification Search
CPC ..... A01H 5/02; A01H 5/025; A01H 5/12; A01H 5/00
USPC ..... Plt./226, 263.1
See application file for complete search history.

*Primary Examiner* — June Hwu
(74) *Attorney, Agent, or Firm* — Audrey Charles

(57) ABSTRACT

A new and distinct cultivar of *Brugmansia* plant named 'Little Angel', characterized by its semi-double type, white-colored flowers, medium green-colored foliage, moderately vigorous, compact-upright growth habit, is disclosed.

1 Drawing Sheet

Latin name of genus and species of plant claimed: *Brugmansia sauveolens.*

Variety denomination: 'Little Angel'.

BACKGROUND OF THE INVENTION

The present invention relates to a new and distinct cultivar of *Brugmansia* plant botanically known as *Brugmansia sauveolens* and hereinafter referred to by the cultivar name 'Little Angel'.

The new cultivar originated in a controlled breeding program in Guadalupe, Calif. during May 2005. The objective of the breeding program was the development of early to flower *Brugmansia* cultivars having a more compact growth habit.

The new *Brugmansia* cultivar is the result of open-pollination. The female (seed) parent of the new cultivar is a *Brugmansia sauveolens* species selection, not patented, characterized by its single-type, white-colored flowers, dark green-colored foliage, and a very vigorous, upright growth habit. The male (pollen) parent of the new cultivar is unknown. The new cultivar was discovered and selected as a single flowering plant within the progeny of the above stated open-pollination during July 2006 in a controlled environment in Guadalupe, Calif.

Asexual reproduction of the new cultivar by terminal stem cuttings since July 2006 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Little Angel' as a new and distinct cultivar of *Brugmansia* plant:

1. Semi-double type, white-colored flowers;
2. Medium green-colored foliage;
3. Moderately vigorous, compact-upright growth habit.

Plants of the new cultivar differ from plants of the female parent primarily in flower-type, shade of foliage color, and growth vigor.

Of the many commercially available *Brugmansia* cultivars, the most similar in comparison to the new cultivar is 'Double Angel's Trumpet', not patented. However, in side-by-side comparison, plants of the new cultivar differ from plants of 'Double Angel's Trumpet' in at least the following characteristics:

1. Plants of the new cultivar are shorter, as measured at first flower, than plants of 'Double Angel's Trumpet';
2. Plants of the new cultivar have lighter green-colored foliage than plants of 'Double Angel's Trumpet'; and
3. Plants of the new cultivar have a flower type different from plants of 'Double Angel's Trumpet'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Little Angel'. The plants were grown in 12-inch pots for 9 weeks in a greenhouse at West Chicago, Ill. Plants were given one pinch at transplant.

DETAILED BOTANICAL DESCRIPTION

Figure 1:
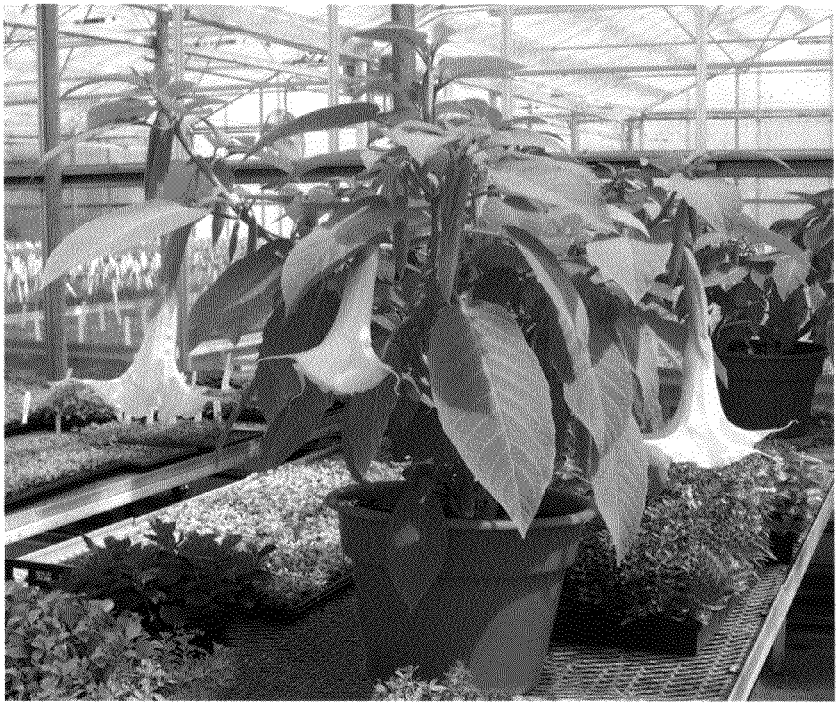
FIG. 1 illustrates a side view of the overall growth and flowering habit of 'Little Angel'.
Figure 2:
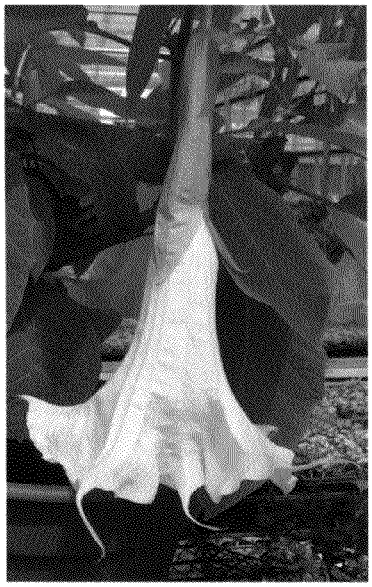
FIG. 2 illustrates a close-up view of an individual flower of 'Little Angel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 12-inch pots for 9 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Brugmansia sauveolens* cultivar Little Angel.

Parentage:

*Female parent*.—*Brugmansia sauveolens* species selection, not patented.

*Male parent*.—Unknown.

Propagation:

*Type cutting*.—Terminal stem.

*Time to initiate roots*.—Approximately 7 to 10 days.

*Time to produce a rooted cutting*.—Approximately 4 to 8 weeks.

*Root description*.—Fibrous.

*Rooting habit*.—Freely branching, vigorous.

Plant description:

*Commercial crop time*.—Approximately 3 to 4 months from a rooted cutting to finish in a 1 gallon container.

*Growth habit and general appearance*.—Moderately vigorous, compact-upright.

*Size*.—Height from soil level to top of plant plane: Approximately 70.0 cm. Width: Approximately 120.0 cm.

*Branching habit*.—Freely branching, pinching enhances basal branching. Quantity of main branches per plant: Approximately 4.

*Branch*.—Strength: Strong, becomes woody with age. Length: Approximately 50.0 cm. Diameter: Approximately 1.5 cm. Length of central internode: Approximately 9.0 cm. Texture: Densely pubescent. Color of young stems: 144A. Color of mature stems: 199D with 144A visible through longitudinal fissures.

Foliage description:

*General description*.—Quantity of leaves per main branch: Approximately 6. Fragrance: None detected. Form: Simple. Arrangement: Alternate.

*Leaves*.—Aspect: Petiole is at an acute angle to stem, leaf blade becomes pendulous with age. Shape: Elliptic. Margin: Entire. Apex: Acute. Base: Rounded or oblique. Venation pattern: Pinnate. Length of mature leaf: Approximately 28.0 cm. Width of mature leaf: Approximately 13.0 cm. Texture of upper and lower surfaces: Densely pubescent with a mixture of glandular and non-glandular hairs. Color of upper surface of young and mature foliage: Closest to between 137A and 137B with venation of 146B. Color of lower surface of young and mature foliage: Closest to 147B with venation of 147C.

*Petiole*.—Length: Approximately 9.5 cm. Diameter: Approximately 5.0 mm. Texture: Densely pubescent. Color: 146B.

Flowering description:

*Flowering habit*.—'Little Angel' is freely flowering under outdoor growing conditions with substantially continuous blooming from spring through autumn and year-round in greenhouse environment.

*Lastingness of individual flower on the plant*.—Approximately 7 to 10 days.

Flower description:

*General description*.—Type: Semi-double, funnelform, pendulous, self-cleaning. Quantity per plant: Approximately 5. Fragrance: Heavily fragrant in evenings.

*Bud*.—Rate of opening: Generally takes 4 to 5 days for bud to progress from first color to fully open flower. Quantity per plant: Approximately 21.

*Bud just before opening*.—Shape: Narrowly oblong. Length: Approximately 14.0 cm. Diameter: Approximately 2.0 cm. Texture: Densely pubescent with a mixture of glandular and non-glandular hairs. Color: Closest to 144A.

*Corolla*.—Vertical axis: Approximately 34.0 cm. Horizontal axis: Approximately 26.0 cm.

*Lobes*.—Quantity: 5, fused to form a tube, and two to three irregularly-shaped petaloids. Shape: Fan. Margin: Entire, undulating. Apex: Acuminate with extended and recurved point of approximately 4.5 cm in length and 1.0 mm in width. Length from tube excluding point: Approximately 6.5 cm. Width: Approximately 15.0 cm. Texture of outer surface: Sparsely glandular pubescent on venation. Texture of inner surface: Glabrous. Color of outer surface when first open: 2D. Color of inner surface when first open: 155D. Color of outer and inner surfaces when fully open: NN155B.

*Corolla tube*.—Length: Approximately 16.5 cm. Diameter at distal end: Approximately 8.0 cm. Diameter at proximal end: Approximately 1.2 cm. Texture of outer surface: Densely glandular pubescent on venation. Texture of inner surface: Glabrous. Color of outer surface when first open: 2D. Color of inner surface when first open: 155D. Color of outer and inner surfaces when fully open: NN155B and 145D under sepals.

*Sepals*.—Quantity per flower: 5, fused. Shape: Linear. Margin: Entire, split to form two lobes. Apex: Acute. Length: Approximately 18.5 cm. Width: Approximately 1.5 cm. Texture of outer surface: Densely pubescent with a mixture of glandular and non-glandular hairs. Texture of inner surface: Sparsely pubescent. Color of outer and inner surfaces: Closest to 144A.

*Peduncle*.—Strength: Strong. Aspect: Obtuse angle to stem. Length: Approximately 5.5 cm. Diameter: Approximately 6.0 mm. Texture: Densely glandular pubescent. Color: 146C.

*Reproductive organs*.—Androecium: Stamen quantity: 5, filaments adnate to corolla. Stamen length: Approximately 19.2 cm. Filament length: Approximately 16.0 cm. Filament color: 145D. Anther shape: Bilobed, oblong. Anther length: Approximately 3.2 cm. Anther texture: Densely pubescent. Anther color: 156A. Pollen amount: Abundant. Pollen color: 155A.

Gynoecium: Pistil quantity: 1 per flower. Pistil length: Approximately 20.0 cm. Stigma shape: Two-lobed, fused. Stigma length: Approximately 9.0 mm. Stigma color: 158D. Style length: Approximately 17.8 cm. Style color: NN155B. Ovary length: Approximately 1.3 cm. Ovary color: 144D.

Seed and fruit production: Neither seed nor fruit production has been observed.

Disease and pest resistance: Resistance to pathogens and pests common to *Brugmansia* has not been observed.

What is claimed is:

1. A new and distinct cultivar of *Brugmansia* plant named 'Little Angel', substantially as herein shown and described.

* * * * *